(12) United States Patent
Yancey, Jr.

(10) Patent No.: US 7,853,407 B2
(45) Date of Patent: Dec. 14, 2010

(54) SYSTEM FOR IMPROVING ANTIBIOTIC USE IN ACUTE CARE HOSPITALS

(75) Inventor: Robert W. Yancey, Jr., Gainesville, FL (US)

(73) Assignee: Bluarc Health LLC, Gainesville, FL (US)

(*) Notice: Subject to any disclaimer, the term of this patent is extended or adjusted under 35 U.S.C. 154(b) by 1139 days.

(21) Appl. No.: 11/031,298

(22) Filed: Jan. 6, 2005

(65) Prior Publication Data
US 2005/0182303 A1   Aug. 18, 2005

Related U.S. Application Data

(60) Provisional application No. 60/534,649, filed on Jan. 6, 2004.

(51) Int. Cl.
G01N 33/48 (2006.01)
C12M 1/00 (2006.01)
C12Q 1/00 (2006.01)
G01N 31/00 (2006.01)
G06G 7/48 (2006.01)

(52) U.S. Cl. .................. 702/19; 703/11; 702/22; 435/4; 435/283.1

(58) Field of Classification Search ............ None
See application file for complete search history.

(56) References Cited

PUBLICATIONS

Barriere, S. L. et al., "The Role of the Pharmacist in Antimicrobial Agent Therapy," *J. Infect. Dis.*, (1989), 159(3):593-594.
Bryan, C. S. et al., "Analysis of 1,186 Episodes of Gram-Negative Bacteremia in Non-University Hospitals: The Effect of Antimicrobial Therapy," *Rev. Infect. Dis.* (1983), 5(4):629-638.
Doern, G. V. et al., "Clinical Impact of Rapid in Vitro Susceptibility Testing and Bacterial Identification," *J. Clin. Microbiol.* (1994), 32(7):1757-1762.
Dunagan, W. C. et al., "Anticirobial Misuse in Patients With Positive Blood Cultures," *Am. J. Med.* (1989), 87:253-259.
Evans, R. S. et al., "Improving Empiric Antibiotic Selection Using Computer Decision Support," *Arch. Inter. Med.* (1994), 154:878-884.
Gerding, D. N. et al., "Aminoglycoside Resistance and Aminoglycoside Usage: Ten Years of Experience in One Hospital," *Antimicrobial Agents and Chemotherapy* (1991), 35(7):1284-1290.
Goldman, D. A. et al., "Strategies to Prevent and Control the Emergence and Spread of Antimicrobial-Resistant Microorganisms in Hospitals," *JAMA* (1996), 275(3):234-240.
Gums, J. G. et al., "A Randomized, Prospective Study Measuring Outcomes After Antibiotic Therapy Intervention by a Multidisciplinary Consult Team," *Pharmacotherapy* (1999), 19(12):1369-1377.
Leibovici, L. et al., "Monotherapy Versus Beta-Lactam-Aminoglycoside Combination Treatment for Gram-Negative Bacteremia: A Prospective, Observational Study," *Antimicrobial Agents and Chemotherapy* (1997), 41(5):1127-1133.
Lesar, T. S. et al.,"Survey of Antibiotic Control Policies in University-Affiliated Teaching Institutions," *Ann. Pharmacother.* (1996), 30:31-4.
Maki, D. G. et al., "A Study of Antimicrobial Misuse in a University Hospital," *Am. J. Med. Sci.* (1978), 275:271-282.
Marr, J. J. et al., "Guidelines for Improving the Use of Antimicrobial Agents in Hospitals: A Statement by the Infectious Diseases Society of America," *J. Infect. Dis.* (1988), 157(5):869-876.
Perstotnik, S. L. et al., "Implementing Antibiotic Practice Guidelines Through Computer-assisted Decision Support: Clinical and Financial Outcomes," *Ann. Intern. Med.* (1996), 124:884-890.
Quintiliani, R. et al., "Economic Impact of Streamlining Antibiotic Administration," *Am. J. Med.* (1987), 82(suppl 4A):391-394.
Rifenburg, R. P. et al., "Benchmark Analysis of Strategies Hospitals Use to Control Antimicrobial Expenditures," *Am. Health-Syst. Pharm.* (1996), 53(17):2054-2062.
White, Jr. et. al., "Effects of Requiring Prior Authorization for Selected Antimicrobials; Expenditures, Susceptibilities, and Clinical Outcomes," *Clin. Infect. Dis.* (1997), 25:230-239.
Yu, V. L. et al., "Antimicrobial Selection by Computer," *JAMA* (1979), 242(12):1279-1282.

*Primary Examiner*—Eric S DeJong
(74) *Attorney, Agent, or Firm*—Saliwanchik, Lloyd & Saliwanchik (57) ABSTRACT

The present invention provides systems and methods for improving the administration and usage of antibiotic/antimicrobial regimens. The method and system of the invention includes (a) establishing a multidisciplinary antimicrobial treatment team; (b) obtaining patient data; (c) reviewing patient data for sub-optimal antibiotic regimens and when necessary, conferring if MATT members regarding regimen recommendations; (d) generating reports with recommendations for optimal antibiotic regimens based on the review of the patient data.

11 Claims, 1 Drawing Sheet

Fig. 1

SYSTEM FOR IMPROVING ANTIBIOTIC USE IN ACUTE CARE HOSPITALS

CROSS-REFERENCE TO A RELATED APPLICATION

This application claims the benefit of U.S. Provisional Application Ser. No. 60/534,649, filed Jan. 6, 2004.

BACKGROUND OF THE INVENTION

Infectious diseases are a major cause of morbidity and mortality and contribute substantially to health care costs in the United States. Infections account for approximately 30% of hospital admissions. In particular, septicemia, pneumonia, acute respiratory infections, cellulitis, and abscesses account for a substantial number of hospital admissions. Ranked fifth as an underlying cause of death in 1980, infectious diseases have risen to the third-ranked cause of death in the last several years, just behind cardiovascular disease and malignancies.

An estimated 26-53% of hospitalized patients receive at least one antibiotic. Kunin, C. M., "Problems in antibiotic usage," in Mandell G. L. et al. *Principles and practice of infectious diseases*, 3$^{rd}$ ed., John Wiley & Sons, 427-34 (1989); Maki, D. G. and A. Schuna, "A study of antimicrobial misuse in a university hospital," *Am. J. Med. Sci.*, 275:271-82 (1978); and Bryan, C. S. et al., "Analysis of 1,186 episodes of gram-negative bacteremia in non-university hospitals: the effect of antimicrobial therapy," *Rev Infect Dis*, 5:629-36 (1983). Timely and appropriate antibiotic administration improves survival in patients with serious infections. Pestotnik, S. L. et al., "Implementing antibiotic practice guidelines through computer-assisted decision support: clinical and financial outcomes," *Ann Intern Med.*, 124:884-90 (1996); Evans, R. S. et al., "Improving empiric antibiotic selection using computer decision support," *Arch Intern Med.*, 154: 878-84 (1994).

Unfortunately, antimicrobial therapy for these patients is often inappropriate. Errors in dosing and selection of antimicrobial therapy are common. For example, it is estimated that 22-40% of antibiotic prescriptions are incorrect. Yu, V. L. et al., "Antimicrobial selection by computer," *JAMA*, 242:1279-82 (1979); Dunagan, W. C. et al., "Antimicrobial misuse in patients with positive blood cultures," *Am J Med*, 87:253-9 (1989); and Byl, B. et al., "Risk factors for inappropriate antimicrobial therapy of bacteremia, relation to the outcome," in *Program and abstracts of the 38$^{th}$ interscience conference on antimicrobial agents and chemotherapy*, Wash., D.C., American Society for Microbiology, (1998). Such inappropriate therapy is associated with increased patient mortality, adverse drug reactions, increased hospital costs, and emergence of multiple drug-resistant bacteria.

The major cause of inappropriate antibiotic therapy is the complexity of the prescribing process. There are more than 90 parental and oral antibiotics from which to choose. When prescribing antibiotics, clinicians must consider a bewildering array of data including an antibiotic's pharmacokinetic profile, relative efficacy, toxicities, local resistance patterns, drug-drug interactions, patient allergies, and drug costs. Other considerations are the site of infection, likely microorganisms present and their usual antimicrobial sensitivity patterns, patient alterations in renal, cardiac, and hepatic function; and the severity of the patient's illness. Therefore, it is difficult for clinicians who are not extensively trained in the administration of antimicrobial agents to make correct choices.

A number of approaches to solving the problem of suboptimal antibiotic therapy have been attempted, including formulary restriction, drug utilization review, rapid reporting of culture and susceptibility reports, computer-based decision support, and pharmacy intervention programs. Pestonik, S. L. et al., "Implementing antibiotic practice guidelines through computer-assisted decision support: clinical and financial outcomes," *Ann Intern Med.*, 124:884-90 (1996); Lesar T. S. and L. L. Briceland," Survey of antibiotic control policies in university-affiliated teaching institutions," *Ann Pharmacother*, 30:31-4 (1996); Rifenburg, R. P. et al., "Benchmark analysis of strategies hospitals use to control antimicrobial expenditures," *Am Health-Syst Pharm*, 53(17):2054-62 (1996); Goldman, D. A. et al., "Strategies to prevent and control the emergence and spread of antimicrobial-resistant microorganisms in hospitals," *JAMA*, 276:234-40 (1996); Quintiliani, R. et al., "Economic impact of streamlining antibiotic administration," *Am J Med*, 82(suppl 4A):391-4 (1987); and Doem, G. V. et al., "Clinical impact of rapid in vitro susceptibility testing and bacterial identification," *J Clin Microbiol*, 32:1757-62 (1994). Formulary changes within a drug class seldom produce meaningful differences in patient disease outcomes, and restrictive formularies achieve only modest cost savings by themselves. Drug utilization reviews seldom affect outcomes because they occur long after the prescribing event. Sophisticated computerized decision-support programs can be effective but are expensive and not available for general use. Rapid microbiology reports may result in savings but only partly address the problem of inappropriate antimicrobial therapy. In another large, prospective, observational study, it was reported that mortality was nearly halved when appropriate antibiotics were administered. Leibovici, L. et al., "Monotherapy versus β-lactam-aminoglycoside combination treatment for gram-negative bacteremia: a prospective, observational study," *Antimicrob Agents Chemother*, 41:1127-33 (1997). It would follow that any system that would improve antibiotic selection would improve sepsis mortality.

In 1988, the Infectious Diseases Society of America (IDSA) developed guidelines for improving the use of antimicrobials in hospitals. The society suggested the creation of antimicrobial teams to improve antimicrobial use. See Marr, J. J. et al., "Guidelines for Improving the use of antimicrobial agents in hospitals: a statement by the Infectious Diseases Society of America," *J Infect Dis*, 159-593-4 (1989). Prohibitive factors such as associated expenses, time, manpower, and equipment necessary to plan and implement such teams have prevented hospital administrators from further developing the teams to their potential.

Although systems to improve antibiotic use, such as those described above, have been applied in many hospitals all over the world, the vast majority of these systems have failed to substantially improve antimicrobial usage. The reasons for the failures are myriad. Even if these teams are funded and implemented, the difficulty remains in the timing of the delivery of information from these teams to the clinician at the actual time of antibiotic prescription. Generally speaking, these systems are heavy handed and slow, and are often antagonistic to the physician. In general, these teams have not achieved their potential results largely due to clinician resistance to pharmacy recommendations because they are often clinically irrelevant or delayed.

A randomized study performed at Alachua General Hospital in Gainesville, Fla. (see Gums, J. G., Yancey R. W. et al., "A Randomized, Prospective Study Measuring Outcomes after Antibiotic Therapy Intervention by a Multidisciplinary Consult Team," *Pharmacotherapy*, 19(12):1369-1377

(1999)) demonstrated that optimizing antibiotic use results in more rapid patient discharge and improved survival. Furthermore, the study demonstrated that a high level of physician acceptance (86%) could be obtained if multidisciplinary team advice was carefully crafted and monitored to be clinically relevant and timely.

In this study, a team consisting of an infectious diseases specialist, a specially trained pharmacist, and the microbiology laboratory, was assembled to determine if the multidisciplinary team approach to antimicrobial usage would improve patient outcomes. Specifically, the team was assigned to address antimicrobial usage in a select patient population receiving suboptimal intravenous antibiotics after the initial prescription. The study results revealed that a team approach would be useful in reducing costs associated with intervention and length of stay on a case-by-case basis. There was no discussion, however, as to how to implement the team approach in the hospital as a whole, of using the team in the actual time of the antibiotic prescriptions, nor of using the comprehensive process to control resistant bacteria.

BRIEF SUMMARY OF THE INVENTION

The subject invention provides systems and methods for improving antibiotic/antimicrobial administration and usage. The systems and methods are designed for use in an organizational environment, in particular, in a healthcare-related entity. The systems and methods of the invention comprise: (a) a multidisciplinary antimicrobial therapy team (MATT); (b) compilation and analysis of clinical patient data; (c) compilation and analysis of hospital ecology; (d) generation of at least one report including recommendations regarding optimal antibiotic therapy regimens; and (e) dissemination of the report to a physician utilizing a communication mode selected by the physician.

Accordingly, the present invention uses a multidisciplinary team approach to antimicrobial/antibiotic usage on a case-by-case basis as well as on a global level. In general, multidisciplinary team members (i.e., pharmacist, infectious diseases specialist, and microbiologist) are responsible for such tasks as, and not limited to, identifying those patients whose current antimicrobial/antibiotic regimens are sub-optimal, providing data regarding antimicrobial/antibiotic resistance; and suggesting optimal antimicrobial regimens to be administered.

In particular, the system of the subject invention achieves improved antimicrobial/antibiotic administration and usage by facilitating rapid communication of useful recommendations to the healthcare provider from multidisciplinary team members. The system achieves a more comprehensive improvement in antimicrobial usage patterns by ensuring antibiotic usage is monitored starting from the physicians' initial antibiotic prescription and by providing recommendations to the physician in an easy to accept, convenient manner.

In one embodiment, the decision for the appropriate antibiotic/antimicrobial regimen to be administered to a patient is made by a physician/clinician. According to the present invention, the decision making process is improved through enhancements in the information and in the speed in which the information is provided to the physician/clinician. These enhancements are achieved, at least in part, by the cooperative efforts between the multidisciplinary team members to pool and interpret the necessary information for the physician/clinician and to communicate rapidly and efficiently the enhanced information. Introducing such cooperative efforts in a computerized environment further enhances the quality of information and speed of information disseminated to the physician. Such enhanced communication and information enables the physician to make consistently better choices in prescribing antimicrobials/antibiotics than previously allowed.

In another embodiment, the decision for the appropriate antibiotic/antimicrobial to be administered to a patient is made automatically using the systems and methods of the invention. In a related embodiment, the most optimal antibiotic regimen recommended by the systems and methods of the invention is selected and automatically administered to a patient, without physician input.

As a result of the implementation of the system of the subject invention, improvements in healthcare can be achieved. These improvements can include, but are not limited to, improved patient recovery, shorter hospital stays, reduced costs of treatment, and a reduction in drug-resistant pathogens.

In carrying out the above objectives of the present invention, a method is provided for analyzing patient data to detect sub-optimal antibiotic regimens. The method includes the steps of establishing a multidisciplinary team for addressing patient antibiotic regimens; reviewing patient cultures and analyzing patient data after the patient has initiated an antibiotic regimen, determining preferred antibiotic regimens based on the analysis; generating at least one report with the recommended preferred antibiotic regimens; and communicating the report to the attending physician in accordance with the attending physician's communication preferences.

In a preferred embodiment, communication between the team members, in particular with the physician, occurs rapidly so as to effectively provide antimicrobial/antibiotic therapy for the individual patient. Most preferably, communication between team members occurs at the moment of the initial antibiotic prescription or at the moment in which new information is available regarding the current prescription. The system is designed to improve antimicrobial use not in just the individual patient but also system wide. As the system begins to generally affect hospital-wide antibiotic usage, it will then begin to affect the hospital-wide occurrence of resistant bacteria.

The system provides opportunity for anti-microbial cycling or mixing, which are systems to prevent the stereotypical use of the same antibiotics over and over in the same hospital or ward. Antimicrobial cycling has been demonstrated to be an effective method to reduce the occurrence of individual strains of resistant bacteria (White, Jr, et. al., "Effects of requiring prior authorization for selected antimicrobials; expenditures, susceptibilities, and clinical outcomes," *Clin Infect Dis,* 25:230-9 (1997) and Gerding et. al., "Aminoglycoside resistance and aminoglycoside usage: ten years of experience in one hospital," *Antimicrob Agents and Chemoth,* 35:1284-90 (1991)). However anti-microbial cycling is cumbersome to administer and may not be effective for the more general problem of bacterial resistance in the hospital.

Antibiotic mixing is a system by which equally efficacious antibiotic classes are randomly assigned to individual patients to prevent the encouragement of resistant bacterial clones. Mathematical models predict that antimicrobial mixing may be a more effective means for controlling resistant bacteria (Bergstrom, Conn., *Proc Nat Acad Sciences,* 101; 36:13285-13290). The systems and methods of the invention provide a means to conveniently provide both anti-microbial cycling and anti-microbial mixing in the hospital, a capability provided by no other previous simple programs. In certain embodiments of the invention, antibiotic mixing and antibiotic cycling are taken into account when analyzing data and generating the recommended antibiotic regimens.

Unlike previous attempts to improve antibiotic usage in hospitals, the system of the subject invention improves general treatment of infections by the very educational nature of communications between key individuals in the acute care setting. As physicians gain comfort, acceptance, and understanding of the system of the invention, the hospital gains more control of general antibiotic usage, preventing the proliferation of resistant bacteria.

The educational nature of the subject invention further improves the general treatment of infections by improving early detection and treatment of serious infections, improving patient survival, and shortening patient length of stay. Unlike other antimicrobial control and stewardship programs, the system of the invention does not attempt to dictate to physicians/clinicians their antimicrobial choice, but merely to educate physicians regarding hospital ecology and antimicrobial pharmacokinetics as they relate to the individual patient. The information is presented in such a way to be of obvious and immediate clinical relevance at the point of usage.

In one embodiment, the system provides for the installation within the hospital of a means to quickly detect patients who may need: antibiotics; a change in antibiotics; or an evaluation of possible sepsis (also referred to herein as the 'Early ID' system). It has been repeatedly demonstrated, and is generally accepted, that earlier administration of appropriate antibiotics results in better outcomes in infected patients. The Early ID system of the invention does not wait for the physician to review new culture results or for the physician to recognize that the patient has had a change in his clinical status indicating a new or deteriorating infection. Rather, the Early ID system of the invention trains nurses and pharmacist to gather data and interpret it for the physician/clinician in advance of visitation and review of a patient's clinical condition (also known to the skilled artisan as "rounds" or "rounding of patient") and quickly transmits the interpretation from the nurses/pharmacist to the physician/clinician as soon as the new information or interpretation is available.

Another embodiment of the subject invention includes a program storage device (Sepsis Tree Decision Support Program and Database) readable by a machine (such as a computer) and tangibly embodying a program of instructions executable by the machine to perform the method steps of the invention. These method steps are carried out as follows: collection (such as by automated interface with the hospital information system and/or by direct clinical data entry by trained bedside nurses) of patient data (e.g., microbiology cultures, fever patterns); selectively sorting the patient data as to their seriousness or priority; printing out patient data reports to a member of the multidisciplinary team responsible for analysis; if a preferred antibiotic regimen is available and communication via the machine is appropriate, entering recommendations into the machine; and transferring the recommendations to the physician/clinician by the method preferred by the individual physician. In certain embodiments, the program storage device performs the step of analyzing the patient data and providing reports to MATT and/or the physician regarding recommendations for optimal antibiotic regimens.

A key feature of the system is the individualized means of reporting recommendations to the physicians. Each individual physician has a preferred means of receiving reports on patient data and recommended antibiotic regimens and the system makes efforts to tailor the means of communication to the individual physician's preferences, better assuring a positive response to information.

DETAILED DESCRIPTION OF THE FIGURES

DETAILED DISCLOSURE OF THE INVENTION

The present invention provides systems and methods for reliable and rapid administration of effective antimicrobial/antibiotic therapeutic regimens to patients for improving patient outcomes, and for discouraging the development of resistant microbial strains. The systems and methods of the invention are preferably implemented in one of a variety of known general purpose or special purpose computing system environments. Those of ordinary skill in the art will appreciate that any of a variety of components and interconnections are well-known, and details concerning the construction need not be disclosed in connection with the present invention.

In one embodiment, a method in a computing environment for affecting therapeutically effective antibiotic/antimicrobial regimens is provided. Methods of the invention include the following steps: (a) establishing a multidisciplinary antimicrobial therapy team (MATT); (b) obtaining patient data relevant to the patient's proposed or current antibiotic treatment regimen; (c) reviewing patient data and researching preferred antibiotic/antimicrobial therapy regimens based on the patient's data and hospital ecology (d) generating a report with recommendations for antibiotic regimens based on the review of the patient data; and (e) disseminating the findings and recommendations regarding the antibiotic regimen to the patient's attending physician along with a rationale for the recommendation (the educational component).

The present invention facilitates communication between a physician/clinician and a multidisciplinary team of individuals; communication between individuals within a multidisciplinary team; as well as communication between such teams in an organizational structure, to detect sub-optimal antibiotic regimens and identify/recommend optimal, or at least improve, antibiotic regimens to be administered to a patient.

In a preferred embodiment, the systems and methods of the invention include the step of establishing communication protocols in which communication between team members and the physician are customized to an individual physician's/clinician's preferences. For example, where a physician prefers information/data be relayed via the Internet, protocols are established in which team members electronically transmit information/data regarding antimicrobial usage to the attending physician. In another example, where the physician prefers telephonic or oral communication, protocols are established in which team members provide information/data to the physician either via the telephone or in person. By customizing communication channels based on physician preferences, information/data between team members are efficiently compiled, transmitted, and assimilated to ensure comprehensive analysis and disclosure of antimicrobial/antibiotic usage.

Communications by the system of the invention with the physician/clinician occur during 4 possible stages in the patient's clinical course: (a) the point at which the physician/clinician has determined that antimicrobial therapy is necessary and a specific antibiotic regimen is to be chosen; (b) the point in which a new, clinically important change in condition (i.e., that which would necessarily change antimicrobial therapy) or microbiology laboratory report is made available (e.g., a new positive blood culture or a new microbiology sensitivity report); (c) the point at which the patient's antimicrobial regimen can be safely simplified or streamlined; and/or (d) a potential adverse reaction by the patient to an antibiotic has been identified.

In one embodiment, a means for monitoring antibiotic/antimicrobial usage patterns in the hospital in the form of a database and a means for correlating that database with hospital bacterial resistance patterns are provided in the systems and methods of the invention.

As used herein, the terms "antimicrobial" and "antibiotic" are used interchangeably. The terms antimicrobial or antibiotic describe a substance that can kill or inhibit the growth of microorganisms.

The term "patient," as used herein, describes an organism, including mammals, to which antibiotic treatment with the systems and methods of the invention are provided. Mammalian species that benefit from the disclosed systems and methods for improving antibiotic usage include, and are not limited to, humans, apes, chimpanzees, orangutans, moneys; and domesticated animals (i.e., pets) such as dogs, cats, mice, rats, guinea pigs, and hamsters.

The terms "physician" and "clinician" are used interchangeably. The terms physician or clinician describe an individual who provides health care to a patient. Examples of physicians or clinicians of the invention include, but are not limited to, an individual who has a medical doctorate, a nurse, a nurse practitioner, a physician's assistant, and the like.

Figure 1:
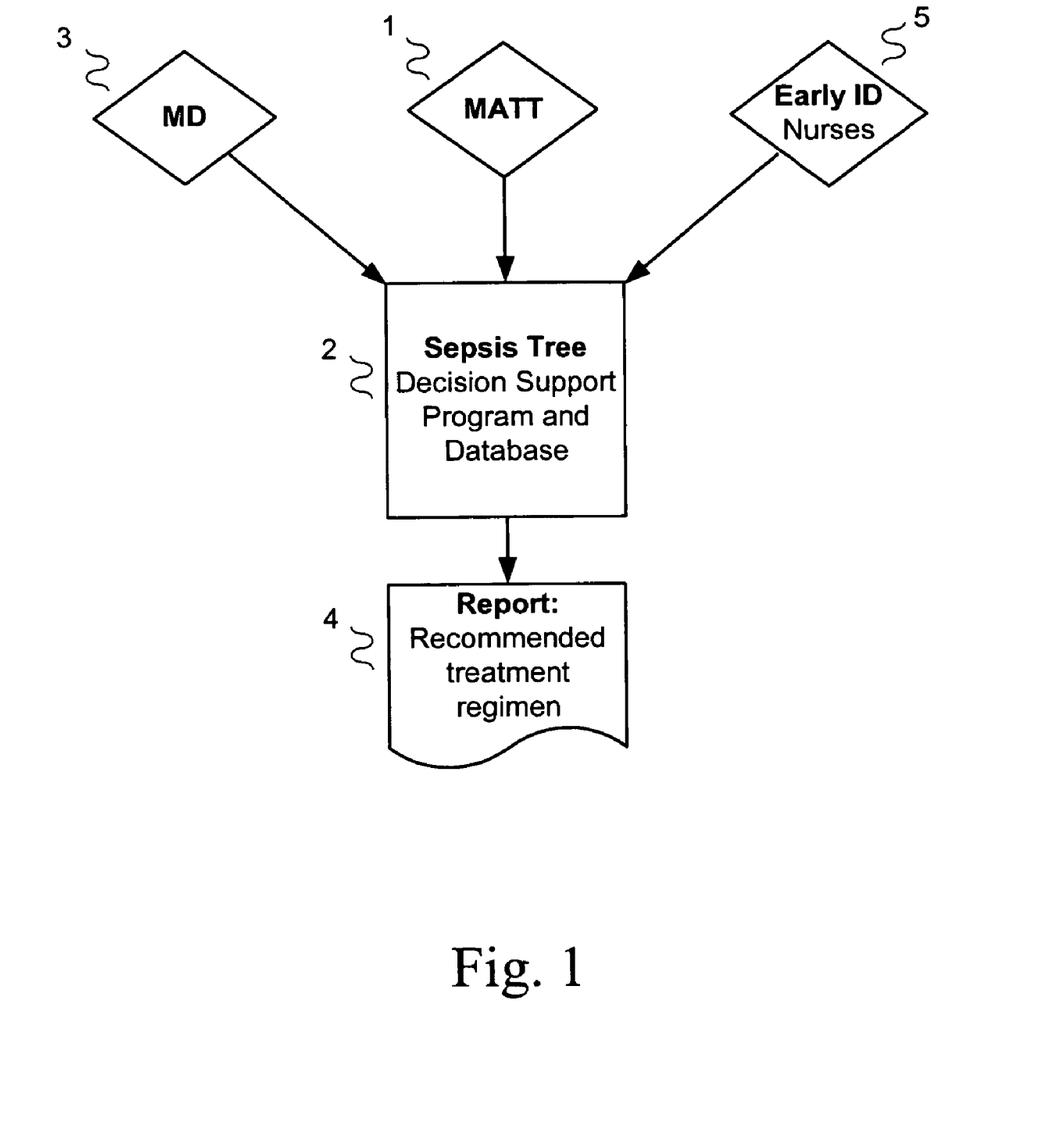
FIG. 1 is a diagram representing the overall system structure of one embodiment of the invention.

A hospital-based application of a method for administering preferred antibiotic regimens to patients is illustrated in FIG. 1. In FIG. 1, a multidisciplinary antimicrobial therapy team (MATT) is established 1. The MATT includes individuals who contribute to the process of identifying preferred antibiotic regimens for patients. In one embodiment, the MATT includes individuals with specialized knowledge relating to microbiology, pharmaceuticals, infectious diseases, and medical treatment.

A program storage device, such as a Sepsis Tree decision-support program 2, is the means by which data input by the physician 3 and/or clinician 5 or MATT team member 1 are collated and analyzed to generate recommended antimicrobial regimens 4, preferably in order of most preferred to lease preferred (but acceptable) regimens. In certain embodiments, the Sepsis Tree decision-support program can analyze data regarding patient renal function, patient allergies, hospital antibiotic/antimicrobial resistance patterns and provide recommended antimicrobial regimens based on empiric sepsis category and appropriate standards for antibiotic rotation.

In certain embodiments, the physician 3 can enter patient-specific clinical data for an individual patient (such as renal function or allergies) into the program storage device. In other embodiments, the MATT team members can provide data regarding the microbiology of the patient's infection, clinical data regarding patients (i.e., in an intensive care unit or ICU), data regarding patient laboratory or culture results, data regarding antibiotic prescriptions, data regarding hospital antibiotic resistance patterns, and data regarding references from which recommendations are derived, into the program storage device. Early ID nurses, who include trained registered nurses, also provide clinical patient data to the program storage device, including data regarding new septic patients or new positive blood cultures.

In one embodiment, a report 4 is communicated to a physician/clinician, wherein the report contains clinical data and a listing of preferred antibiotic/antimicrobial regimens along with the rationale behind why the regimens are preferred. In certain embodiments, the report can include patient summary, specific doses of antibiotic(s) to be administered to the patient, alternative prescriptions, rationale for recommended antibiotic regimen, and references supporting the rationale. The report is preferably rapidly communicated to the physician/clinician in a manner preferred by the physician/clinician (i.e., via text message on a beeper).

Various forms of data can be provided to systems and methods of the invention. Such data (or input) can include new microbiology reports; Early ID nurse information on a specific patient's clinical status (such as a change in clinical condition that might indicate a new infection; or an adverse drug reaction); laboratory data (such as patients with new onset leukocytosis; patients with new onset of abnormal renal function or liver function tests); patient medication administration profiles; physician/clinician requests for antibiotic/antimicrobial recommendations; overall hospital antibiotic usage patterns; and adverse antibiotic drug reactions (such as *Clostridium difficile enterocolitis* of drug-induced allergic rashes).

In certain embodiments, a clinician or an Early ID nurse inputs into a program storage device data that cannot be obtained from hospital patient information systems and must be obtained clinically: Such data can include, but are not limited to, nosocomial versus community acquired infection; description of the patient history of possible antibiotic allergies; identification of likely infection source or location (if known) of the infection source; indication that infection source is unknown; and reasoning for why a new antibiotic regimen recommendation is being requested (such as current antibiotic failure; new infection identified; adverse drug reaction; or presence of certain clinical symptoms e.g., dysuria).

Additional data input into a program storage device are obtained either via hospital patient information system or clinician input. Such data can include, but are not limited to, patient height and weight; appearance of wounds; presence of important medical conditions that may affect antimicrobial selection; congestive heart failure; renal insufficiency or an acute decrease in urine output; hematological disorders e.g., leucopenia or thrombocytopenia; important medical conditions that may affect the likely microbiology of an individual patient's infection e.g., diabetes, post operative condition, steroid therapy, mechanical ventilation, HIV, and the like; and shock.

In certain embodiments, MATT members provide data input into a program storage device. Data provided by MATT members include, but are not limited to, antibiotic-drug interactions with the individual patient's current medications as assessed by the MATT pharmacists; microbiology reports; interpretation of culture results (such as contaminated blood culture versus true positive, interpretation of central line tip cultures where the culture report represents colonization versus true infection, and the like); drug of choice given the final identification and sensitivities of infecting bacteria; recommendations of duration of antibiotic therapy based upon the clinical situation; antibiotic streamlining programs; oral medications programs; appropriateness of duration of intravenous antibiotics for bacteremias and endocarditis; adjustments in antibiotic cycling and mixing capabilities, based on hospital epidemiology; and limitation of specific antibiotics based on hospital epidemiology.

The systems and methods of the invention also provide various forms of data output including, but not limited to: (a) a Sepsis Tree generated report to the clinician in a timely and individually preferred manner; and (b) updated antibiotic regimens as the result of reassessment of sepsis tree antibiotic selection criteria and mixing or cycling parameters based upon hospital antibiotic usage patterns and microbial resistance patterns.

In certain embodiments, a report can be generated in a non-computerized environment. For example, the program storage device merely provides a repository for the various forms of data to be provided to the systems and methods of the invention. MATT members can perform the analysis and generate by hand a report for dissemination to the physician. Such noncomputer-generated reports are provided by the MATT members for use in hospitals without computerized information systems or that have incompatible information systems.

In other embodiments, the systems and methods for establishing patient antibiotic regimens can be provided in a computerized environment. In a preferred embodiment, the system of the invention includes: (a) a central server that interfaces with hospital information systems, including computerized patient medication profiles and patient laboratory values; (b) physician or clinician input capability at the sites of patient care, where the input capability can include an easy to use web browser interface and a means for rapid generation of full recommendation; and/or (c) output capability to provide reports to a MATT pharmacist; a MATT physician supervisor; clerical desks of patient care areas; and/or clinicians, via preferred communication modes (such as telephone, facsimile, electronic mail, wireless text messaging, e.g., Blackberry).

The output reports of the computerized systems and methods of the invention can include information regarding: (a) antibiotic regimen recommendations; (b) 1-5 potential antibiotic regimens in order of preference; (c) brief clinical summary of patient and parameters that effect antibiotic selection; (d) rationale for the suggested regimen; and (e) references from the medical literature.

The output function of the invention preferably includes the capability of providing reports: (a) with random or non-random assignment of order of preference of equally efficacious antimicrobial regimens based on hospital epidemiological considerations; (b) on pre-printed order sheet that is signature ready; (c) that are transmitted to the clinician by selected method; (d) of a summary of activity reports; (e) of recommendation acceptance rate by clinicians; (f) including antibiotic prescription/order forms; (g) of antibiotic utilization patterns by clinician, ward, or diagnosis; (h) of adverse drug reactions to antibiotics; (i) of time from antimicrobial prescription to actual administration to the patient; (j) of frequency of the various types of recommendations; and (k) of the correlation of inventive system activity with hospital microbial resistance patterns.

MATT, in accordance with the subject invention, preferably performs any one or combination of the following functions in the systems and methods of the invention: (a) systematic reviews of hospital patient antibiotic profiles; (b) daily rounding of patients with MATT infectious diseases physician in the ICU; (c) systematic review of all microbiology reports as soon as they are made available; (d) review of the antibiotic regimens of all patients with a white cell count of more than 17,000; and (e) review antibiotic regimens of all patients receiving specific targeted antibiotics.

In one embodiment, an Early ID system of the invention provides a means for rapid detection of patients who need antibiotics, a change in antibiotics, or an evaluation of possible sepsis. The Early ID system is implemented to preferably improve outcomes of patients with infections by reliably delivering to the patients the best available antibiotics with all possible speed.

As noted above, current clinical systems await review by a patient's physician, who would then recognize the importance of a change in the patient's clinical condition or the importance of a new culture report. The Early ID system preferably utilizes specially trained, registered nurses to collect patient clinical data to assist the MATT in making timely recommendations to clinicians so as to by-pass current clinical systems.

According to the subject invention, an Early ID system can be established by training a select group of hospital nurses (such as registered nurses) to be Early ID nurses 5. Such Early ID nurses are preferably available 24 hours a day/7 days a week. More preferably, one or two Early ID nurses are available at all times. In certain embodiments, Early ID nurses perform a variety of functions other than collecting patient data including, but not limited to, assisting pharmacists and bedside nurses with interpretation of infection related clinical findings; collecting and entering data in a program storage device such as the Sepsis Tree decision-support database; and interacting with the MATT pharmacists.

In accordance with the subject invention, the Early ID nurse gathers data for input into a program storage device. Such data can be gathered from communication with bedside nurses to help interpret the importance of a new culture report or a change in clinical status of the patient or from personal identification of a problem potentially warranting a new antibiotic prescription. Once the Early ID nurse identifies a situation that might warrant an antibiotic regimen recommendation using the systems and methods of the invention, the Early ID nurse contacts the MATT pharmacist and/or the MATT infectious diseases physician. If the MATT member determines that a new prescription is necessary, data is entered into the Sepsis Tree support unit to generate a recommendation. New recommendation of antimicrobial therapy, generated in a computerized or non-computerized environment, is transmitted to the attending physician so that the patient's problem is addressed quickly and with few errors.

In certain embodiments, the systems and methods of the invention include the step of updating the preferred antibiotic/antimicrobial regimen. The updating step of the invention can include reassessment of patient data relevant to the current antibiotic regimen; reviewing patient data and researching preferred antibiotic therapy regimens based on the patient's data; reviewing hospital ecology; and updating the antibiotic regimen for the patient.

Contemplated individuals that can be included in a MATT include, but are not limited to, an infectious diseases specialist; an infectious diseases-trained pharmacist; a microbiology laboratory liaison; an infection control liaison; and a nursing services liaison.

The infectious diseases specialist, which can include a knowledgeable physician, will preferably have oversight and training responsibilities over the other members of the MATT (such as training of an Early ID nursing team). The infectious diseases specialist also educates and interacts with clinicians.

The infectious diseases-trained pharmacist preferably receives data from the microbiology laboratory, Early ID nurses, and clinicians. The data is analyzed by the infectious diseases-trained pharmacist, who can then generate, with the assistance of a program storage device (such as the Sepsis Tree Decision Support Program and Database), a report communicating antibiotic/antimicrobial regimen recommendations and hospital antibiotic/antimicrobial usage reports. In certain embodiments, the infectious diseases-trained pharmacist alters the program storage device (such as the Sepsis Tree database and decision-support program and database) parameters according to hospital needs as determined by the MATT. More preferably, the infectious diseases-trained pharmacist monitors hospital antibiotic/antimicrobial usage patterns and provides strategies for improving the speed and accuracy of antibiotic administration to the patient.

The microbiology laboratory liaison preferably facilitates the accurate and rapid transfer of microbiology data to the MATT. The microbiology laboratory liaison also alters microbiology laboratory reports to improve the physician's/clinician's ability to interpret data correctly.

The infection control liaison preferably monitors hospital bacterial resistance profiles. More preferably, the infection control liaison informs MATT regarding changes in hospital microbial resistance patterns so as to enable appropriate selection of a therapeutically effective antimicrobial regimen to be delivered to a given patient.

The nursing services liaison preferably assists in the selection and training of Early ID nurses. More preferably, the nursing services liaison provides oversight of Early ID nursing team and ensures the availability of Early ID nurses to physicians/clinicians. Even more preferably, the nursing service liaison trains bedside nurses in the usage of the Early ID nurses.

Once the MATT has been established 1, protocols are developed, including methods of communication between the physician/clinician and other MATT members. Preferably, communication channels are customized to a physician's preference in communication modality (i.e., a system of the invention preferably records an individual physician's preferences as to how he or she would like to receive reports). Non-limiting examples of communication modalities that can be selected by a physician include time of communication such as, morning, evening, specific days of the week (as well as different systems for night time coverage or for covering physicians); form of communication such as written (i.e., print out at a nursing station), telephonic, electronic (i.e., facsimile, electronic mail, next messaging, PDA wireless), and personal communication (i.e., in person with oral report); and the form of report provided (i.e., detailed analysis; summarization; inclusion of specific citations, etc.). In certain embodiments, physicians are provided the capability of supplying electronic signatures so as to minimize delays in initiating antibiotic regimens as well as to ensure rapid selection and administration of the most optimal antimicrobial regimens.

In certain embodiments, the physician is responsible for determining the antibiotic regimen to be administered to an individual patient. In other embodiments, the most preferred antibiotic regimen recommended by either MATT analysis or by a program storage device is administered to an individual patient.

In one embodiment, the physician can provide bedside or laboratory information to a program storage device, including suggestions regarding the appropriateness of the current antimicrobial regimen (i.e., that the regimen is or is not optimal). Once a report is provided to a physician, the physician can either supply a signature, signaling acceptance of the recommended antibiotic regimen or refrain from signing the report in order to signal a rejection of the MATT or Sepsis Tree generated recommendations. In certain embodiments, a physician signature may be requested for an antibiotic order form generated by the Sepsis Tree program. Information from a physician can be provided as feedback to a MATT supervising physician regarding the utility, quality, and format of the sepsis Tree/MATT generated reports. In certain embodiments, a physician can directly initiate a new Sepsis Tree recommendation for a patient by requesting Sepsis Tree suggestions or by entering data directly into the Sepsis Tree input system.

In certain embodiments, the system of the invention is brought into being in stages or even gradually in an acute care setting. In such instances, physicians/clinicians are provided time and opportunity to learn to trust the recommendations of the system and therefore the earliest communications must be of the most obviously clinically helpful types. As the clinicians learn to trust the quality of the communications, they will begin to seek them. They may wish to add patient data themselves and receive recommendations directly from the program. Or they may request that a recommendation be generated for them. Therefore, the system of the invention has flexibility as to who may initiate the antimicrobial recommendation process.

The process for an individual patient prescribing event may also be initiated by a MATT—such as by bedside nursing interaction or a MATT—microbiology interaction and then transmitted to the physician/clinician. Patient data is then obtained using the established protocols. The patient data is then analyzed and, when appropriate, discussed amongst necessary MATT members. MATT members responsible for reporting the results of the analysis then decide, based on the patient data, whether the antibiotic regimen is sub-optimal. Should the antibiotic regimen be considered optimal, no further steps are taken by the MATT members at that time. However, if the patient's antibiotic regimen is sub-optimal, a report is generated with recommendations for improved antibiotic regimens and distributed to the physician per the physician's desired method of communication.

Contemplated protocols to be established amongst the MATT members include, but are not limited to, channels of communication amongst MATT members, including physician preferred method of communication and methods of communication between microbiology, pharmacy, and medical staff; classification and prioritization of patient data; and speed of dissemination of recommendations.

The organizational entity (i.e., hospital) will also establish a means for continuous education programs for team members and other healthcare individuals. The hospital first develops education protocols and compiles a database of intervention and most productive efforts. This database is used in the publication and/or dissemination of information/data regarding antimicrobial usage to other team members and healthcare personnel. The information is also used for JCAHO review. The educational protocols are periodically reviewed for effectiveness and revised when necessary.

In a preferred embodiment, the report generated based on the patient data is comprehensive, addressing all antibiotic use and related epidemiology. More preferably, the report is based on known (and trusted) resources.

The present invention can use general purpose or special purpose computer hardware, including programmable logic devices, to create a computer system or computer sub-system embodying and/or implementing the method of the invention. An apparatus for implementing the invention may be one or more processing systems including, but not limited to, a central processing unit (CPU), memory devices, storage devices, communication links and devices, servers, I/O devices, or any sub-components of one or more processing systems, including software, firmware, hardware or any combination or subset thereof, which embody the invention. User input may be received from the keyboard, mouse, pen, voice, graphical user interface (such as a touch screen), or any other means by which a human can input data into a computer, including through other programs such as application programs.

The current invention also allows transfer of information (such as patient data, data on hospital ecology, or reports) to other computers, for example, using an interface such as PALM™ Corporation's HOTSYNC™ capability. However, other techniques for communicating with other computing platforms can be used, including, for example: infrared, universal serial bus, RS-232, Ethernet, and RF communication methods. In addition, information transfer may be accomplished by various intermediate memory storage devices, such as memory cards, diskettes, or PCMCIA cards. Using HOTSYNC for example, users can both write information to and read information from another computer. To transfer information, the user installs the PDA in a HOTSYNC cradle, exits the invention's program, and presses the HOTSYNC button provided on the PDA. By performing a HOTSYNC, the patient database is automatically transferred to the host computer. After the information is transferred to another computer, the information can be imported into a word processing program for further editing and, preferably, formatted for entry into standard medical logs.

Based on the foregoing specification, the invention may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the invention. The computer readable media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network.

In one embodiment, a computer program product for providing recommendations for optimal antibiotic regiments is provided, where the product includes: computer readable media for providing a patient database comprising patient clinical records; computer readable media for providing a graphical user interface (GUI); computer readable media for providing the capability to allow data input; computer readable media for providing interactive icons to allow entering and editing of said input data; and computer readable media for generating a report by analyzing said input data, wherein said computer readable media for generating a report provides the capability to allow verifying and editing of said report.

In another embodiment, patient data relevant to antibiotic regimen regulation (i.e., microbiology cultures) is entered automatically, or manually, into a database in a computer system accessible to all members of the MATT. Patient data may be entered immediately or at a specified time based on protocols established by members of the MATT or by the organizational entity. Once patient data has been entered, it is selectively sorted (i.e., by seriousness, priority, patient). For example, patients with infections classified by the MATT members as "serious" are immediately made available to the members of the MATT responsible for review and analysis of patient data. After analyzing the patient data and, when necessary, discussing the patient data with relevant MATT members, a report is generated that is provided to the physician with recommendations for a preferred antibiotic regimen.

Significant decreases in length of stay, patient charges, and hospital costs can be achieved using the MATT of the subject invention. Therapeutic benefit is achieved through MATT member compliance and through the comprehensive, multidisciplinary nature of consults. The skilled artisan would readily recognize that there may be multiple preferred antibiotic/antimicrobial regimens available for any one patient case. Thus, in general, interventions are not considered unless a notable improvement in patient status is expected to result from the change in antimicrobial therapy. The multidisciplinary service of the invention functions as an ally in the therapeutic process by facilitating physician consultation with regard to a patient's case. Accordingly, the invention provides an aid to the physician in the decision making process regarding the antibiotic regimen to be administered to a patient.

In accordance with the invention, it is contemplated that the multidisciplinary nature of the interventions accounts for high physician compliance. In essence, the report provided to the physician is a timely expert opinion presented in a non-confrontational manner by at least one MATT member (i.e., a pharmacist) after analysis has been performed, preferably amongst all of the MATT member). This comprehensive approach creates a useful tool for making complex decisions regarding antimicrobial therapy. Through this team effort, physicians receive the latest microbiology data or interpretation of likely microbiology in the clinical syndrome, including recommendations for treatment. In certain instances, it is contemplated that such information will be provided to the physician prior to physician solicitation (such as via the Early ID system).

A further benefit of the present invention is physician education. Physicians implement new prescribing practices in response to reports provided in accordance with the present invention. Thus, institutional antimicrobial therapy is improved with relatively few reports generated by a MATT. Because it has been observed that physicians will generally accept suggestions from the MATT members, the present invention improves antimicrobial therapy.

It is contemplated that the present invention, if applied generally and continually, could help rotate antibiotics systematically and minimize selection of resistant bacteria Vancomycin-resistant Enterococci (VRE), and Methicillin Resistant Staphylococcus aureus (MRSA)). This degree of control of antimicrobial therapy could be applied to epidemics of resistant bacteria and improve hospital-wide sepsis-associated mortality.

The present invention is also cost-effective because it applies existing resources from medical staff, pharmacy, and microbiology laboratory and reallocates a percentage of their time to providing patient care from a multidisciplinary approach.

Much of hospital antibiotic use is empiric; that is, drug choice is based on the clinical syndrome and expected microbiology of the infection rather than on individual culture results. The present invention provides significant benefit to empiric antibiotic therapy selection. Recommendations regarding empiric therapy require more thorough knowledge of infectious syndromes than does merely matching culture results with an antibiotic. Because empiric therapy consults are more difficult than culture-driven consults, a thorough discussion between MATT members, as contemplated by the present invention, can be applied to complex consults and interventions that clinical pharmacists are usually reluctant to attempt without full discussion with infectious disease specialists.

Following is an example that illustrates procedures for practicing the invention. This example should not be construed as limiting.

EXAMPLE

In accordance with the present invention, the following steps can be implemented in one embodiment:
i. Assessing the hospital or healthcare center, including targeting problems areas of antibiotic use, establishing the rate of infectious diseases of interest, and identifying antibiotic/antimicrobial resistant organisms;
ii. Establishing benchmarks (length of stay, credit for each day saved, credit for reduced pharmacy costs, credit for reducing surgical infections);
iii. Establishing case finding methods for the MATT members;
iv. Establishing communication and data collection systems, including the preferred method for communicating with specific attending physicians;
v. Establishing a MATT;
vi. Establishing and implementing protocols, including MATT and attending physician communication regarding patient cases.

In certain embodiments of the invention, any one or combination of the following steps are also performed in order to promote optimal administration of antimicrobial/antibiotic therapeutic regimens:
vii. Improving surgical infection rate by timing prophylactic antibiotics and optimizing preparation procedures;
viii. Controlling the proliferation of antibiotic/antimicrobial resistant organisms by antibiotic rotations;
ix. Educating pharmacists and appropriate physicians to enable the perpetuation of the system and method of the invention;
x. Compiling information for JCAHO reviews;
xi. Compiling in a database the effects of certain types of interventions and most productive efforts;
xii. Publishing or disseminating results and some aspects of techniques; and
xiii. Continuously educating physicians and pharmacists.

All patents, patent applications, provisional applications, and publications referred to or cited herein are incorporated by reference in their entirety to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method for establishing at least one preferred antibiotic regimen for a patient and improving an antibiotic administration regimen at a healthcare facility, wherein the method comprises the steps of:
   (a) obtaining data regarding patients at the healthcare facility;
   (b) processing via one or more suitably programmed computer processing systems the data obtained in step (a) to identify a patient at the healthcare facility for whom at least one preferred antibiotic regimen is to be established;
   (c) processing via the one or more suitably programmed computer processing systems the results obtained from steps (a) and (b) to establish a recommended antibiotic regimen for the patient,
   (d) presenting by the one or more suitably programmed computer processing systems a report for review by a multidisciplinary team, wherein the report comprises the recommended antibiotic regimen for the patient;
   wherein the multidisciplinary team comprises at least two members selected from the group consisting of: an infectious diseases specialist, an infectious diseases-trained pharmacist, a microbiology laboratory liaison, an infection control liaison, and a nursing services liaison, wherein at least one member is a non-physician;
   (e) repeating steps (a) through (d); wherein the repeating step (e) further comprises:
      (i) review of the recommended antibiotic regimen for establishing the at least one preferred antibiotic regimen; and
      (ii) review of the report for consideration in improving the antibiotic administration regimen at the health care facility; and
   (f) communicating the result from step (e) to a clinician who will administer the at least one preferred antibiotic regimen to the patient, via a predetermined preferred communication modality.

2. The method of claim 1, wherein the multidisciplinary team performs any one or a combination of the following functions: systemic reviews of hospital patient antibiotic profiles; daily rounding of patients in the intensive care unit; systemic review of microbiology reports; review of antibiotic regimens of all patients with white cell count of more than 17,000; and review of antibiotic regimens of all patients receiving targeted antibiotics.

3. The method of claim 1, wherein the communication modality takes into consideration at least one factor selected from the group consisting of: time of communication, form of communication, and form of report provided.

4. The method of claim 3, wherein the form of communication to the clinician is selected from the group consisting of: written communication, telephonic communication, electronic communication, and personal communication.

5. The method of claim 1, wherein the data of step (a) is selected from the group consisting of: clinical data regarding the patient, microbiology data of the patient's infection, patient laboratory or culture results; patient medication administration profiles; data regarding hospital ecology; data regarding antibiotic prescriptions and adverse drug reactions, data regarding infection source or location; data regarding hospital antibiotic resistance patterns, data regarding nosocomial infections, data regarding physician requests for antibiotic recommendations, overall hospital antibiotic usage patterns, and data regarding references from which the recommendation is generated.

6. The method of claim 5, wherein the clinical data regarding the patient is any one or combination of the following: patient height, patient weight, appearance of wounds, presence of important medical conditions that may affect antimicrobial selection, identification of any nosocomial infection, congestive heart failure, insufficiency or an acute decrease in urine output, hematological disorders, and important medical conditions that may affect the likely microbiology of a patient's infection.

7. The method of claim 1, wherein communicating the preferred antibiotic regimen is performed at times selected from the group consisting of: a time at which the physician has determined that antimicrobial therapy is necessary and at least one antibiotic regimen is to be chosen; a time at which a new, clinically important change in patient condition is observed; a time at which the patient's microbial regimen can be safely simplified or streamlined; and a time at which a potential adverse reaction by the patient to an antibiotic has been identified.

8. The method of claim 1, wherein the communication of the preferred antibiotic regimen comprises any one or combination of the following: patient clinical data; a listing of preferred antibiotic regimens; a description of rationale for the preferred antibiotic regimens; a patient summary; specific doses of antibiotic(s) to be administered to the patient;

alternative prescriptions; and references supporting the rationale.

9. The method of claim 1, wherein data from step (a) is obtained by at least one registered nurse who collects clinical patient data.

10. The method of claim 1, further comprising the step of administering the at least one preferred antibiotic regimen to the patient.

11. The method of claim 1, wherein patient recovery is improved, hospital stays are shortened, costs of treatment are reduced, and/or proliferation of drug- resistant pathogens is reduced.

* * * * *